United States Patent
Sekine et al.

(10) Patent No.: US 6,192,095 B1
(45) Date of Patent: *Feb. 20, 2001

(54) XENON-133 RADIOACTIVE STENT FOR PREVENTING RESTENOSIS OF BLOOD VESSELS AND A PROCESS FOR PRODUCING THE SAME

(75) Inventors: Toshiaki Sekine; Satoshi Watanabe; Akihiko Osa; Noriko Ishioka; Mitsuo Koizumi; Ryozo Nagai; Akira Hasegawa; Eiichi Okamoto; Akito Miyajima; Keiko Aoyagi; Yoichi Hoshino; Takahiro Yamagishi; Masahiko Kurabayashi, all of Gunma-ken (JP)

(73) Assignee: Japan Atomic Energy Research Institute, Tokyo (JP)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/251,907

(22) Filed: Feb. 19, 1999

(30) Foreign Application Priority Data

Jun. 5, 1998 (JP) .................................................. 10-157566

(51) Int. Cl.[7] .............................. G21G 1/02; G21G 4/04; A61N 5/00; A61N 36/00
(52) U.S. Cl. ................................. 376/189; 376/314; 600/3
(58) Field of Search .................... 600/3; 606/7; 376/189, 376/314

(56) References Cited

U.S. PATENT DOCUMENTS

| | | | |
|---|---|---|---|
| 5,302,168 | * | 4/1994 | Hess . |
| 5,485,835 | * | 1/1996 | Vande Streek et al. ........ 128/205.13 |
| 5,607,442 | * | 3/1997 | Fischell et al. . |
| 5,863,284 | * | 1/1999 | Klein . |
| 5,906,573 | * | 5/1999 | Aretz ........................................ 600/3 |
| 5,919,126 | * | 7/1999 | Armini ..................................... 600/3 |

FOREIGN PATENT DOCUMENTS

19819426 * 11/1999 (DE) .

OTHER PUBLICATIONS

Mallinckrodt Medical, Inc., "Radioactive Gas Solution and Method of Prevention of Restenosis," Research Disclosure, p. 593, May 1998.*

Gillette et al., "Review of Radioisotopes Program, 1964," Oak Ridge National Laboratory, ORNL–3802, pp. 25–26, 52, May 1965.*

Wilson et al., "Preparation of Xenon–133 Radiography Sources from Spent Fuel," Nucleonics, pp. 110–114, Apr. 1958.*

Ikonen et al, "Selective Assessment of Single–Lung Graft Function with Xe–133 Radiospirometry in Acute Rejection and Infection," Chest, V109, N4 (Apr. 1996), pp. 879–884, (abstract only).*

Wagner, H.N., Jr., "Medical Applications of low–energy X–ray and gamma radiation sources," ORNL Proc. of Sump. on Low–Energy X–ray Sources and Gamma Sources and Appl., pp. 239–242, (abstract only), Nov. 1965.*

(List continued on next page.)

Primary Examiner—Charles T. Jordan
Assistant Examiner—K. Kevin Mun
(74) Attorney, Agent, or Firm—Banner & Witcoff, Ltd.

(57) ABSTRACT

Radioactive stents used in angioplasty on sclerotic coronary arteries without the risk of restenosis can be produced by ion injecting $^{133}Xe$ into the surfaces of stents as a nuclide that has a shorter half-life and emits a smaller maximum energy of β-rays than $^{32}p$ Uniform ion injection is accomplished using an apparatus capable of uniform irradiation of the stents with $^{133}Xe$ ion beams. The source of $^{133}Xe$ is a nuclear fission product generated from $^{235}U$ in the fuel rods in nuclear reactor.

1 Claim, 2 Drawing Sheets

OTHER PUBLICATIONS

Kawano et al., "Remnants of 133Xe Radioactivity in a Gas Container," Journal of Health Physics, vol. 21, vo. 4, pp. 262–264, (abstract only), 1986.*

Nagayama, K., "Evaluation of New Methods for Measuring the Hepatic Blood Circulation in Chronic Liver Diseases," Tokyo Jikeikai Ika Daigaku Zasshi, 111(4), pp. 423–440, 1996.*

D'Angelo et al., "Operation Modes of SiCPICal Detector for SPECT Applications," Nucl. Sci. J., 32(5), pp. 413–421, 1995.*

Carter, et al., Effects of Endovascular Radiation From a β–Particle–Emitting Stent in a Porcine Coronary Restenosis Model, *Circulation* 1996; 2364–68.

* cited by examiner

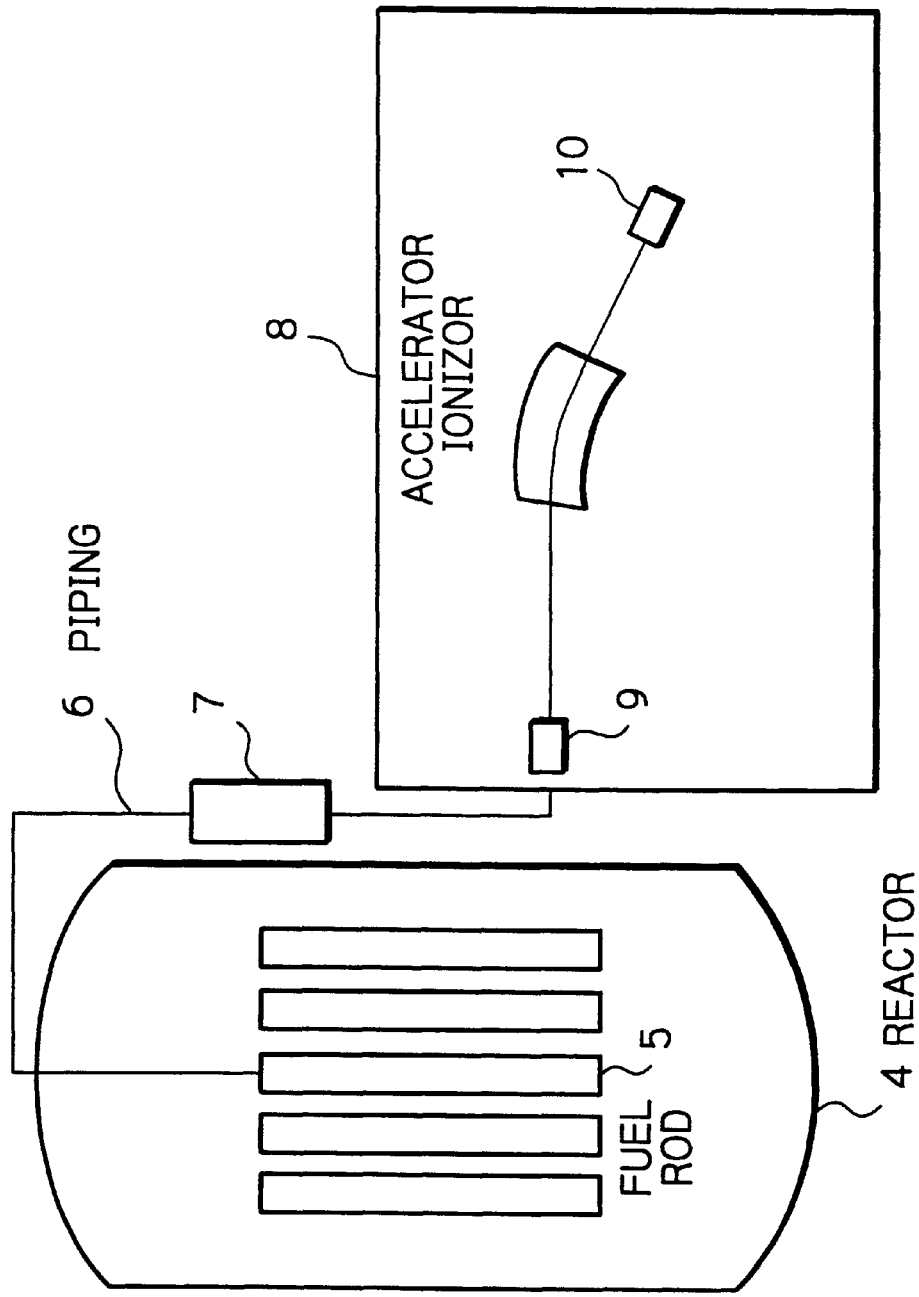

XENON-133 RADIOACTIVE STENT FOR PREVENTING RESTENOSIS OF BLOOD VESSELS AND A PROCESS FOR PRODUCING THE SAME

BACKGROUND OF THE INVENTION

This invention relates to angioplasty as a means of treating arteriosclerosis of coronary arteries. More particularly, the invention relates to a radioactive stent capable of preventing restenosis of blood vessels and a process for producing it.

Stated more specifically, the present invention relates to a radioactive cylindrical stent that has been ion injected with $^{133}$Xe and which will later emit β-rays, γ-rays and internal conversion electrons ejected by γ-decay. The invention also relates to a process for producing the stent. The radioactive stent of the invention is placed within a blood vessel and prevents its restenosis by inhibiting abnormal growth of the smooth muscular cells in it. The advantage of the $^{133}$Xe radioactive stent of the invention is not limited to preventing blockage recurrence after angioplasy with a balloon or an ordinary non-radioactive stent; it can also replace the balloons and ordinary non-radioactive stents commonly used in angioplasy.

To treat arteriosclerosis of coronary arteries, angioplasy is performed using balloons and stents; however, postoperative stenoses often occur and the frequency is 30–40% in the case of using balloons and 10–30% with stents. Opened blood vessels are believed to occlude mainly from abnormal growth of smooth muscular cells and it has recently been found that intravascular exposure to radiations is an effective way to prevent postoperative restenoses (Waksman R. et al., Circulation, 91, (1995) 1533–1539).

One of the ways to implement the intravascular exposure to radiations is by using a stent that has been rendered radioactive on its own and this technique is gaining increasing attention from researchers. However, the only case that has been reported on radioactive stents that are prepared by ion injection is about a β-emitting radioactive stent that has been ion injected with $^{32}$p (Hehrlein C. et al., Circulation, 93, (1996) 641–645).

A problem with this prior art technique is that due to the comparatively long half-life (14.3 days) of $^{32}$p, the time of exposure to the emitted β-rays is unduly prolonged to interfere with the regeneration of vascular endothelia, potentially inducing thrombus formation. Therefore, it is necessary to develop a stent that has been rendered radioactive by means of a shorter-lived radioisotope and which is capable of preventing restenosis of blood vessels without interfering with the regeneration of vascular endothelia.

In addition, in view of the fact that restenosis of a blood vessel occurs in that area of the vessel which is in contact with any surface of the inserted stent, it is required that the entire surface of the stent be uniformly ion injected with a radioactive isotope. Considering the number of patients with arteriosclerosis who are currently under treatment, mass production of radioactive stents is also an important factor.

SUMMARY OF THE INVENTION

According to the present invention, a radioactive stent is produced by injecting $^{33}$Xe as a nuclide that has a shorter half-life and emits a smaller maximum energy of β-rays than $^{32}$p In the invention, a uniform irradiator is employed to enable uniform ion injection into the surface of a stent. Since $^{133}$Xe is a nuclear fission product, an ion injector may be connected to a nuclear reactor to achieve continuous ion injection of $^{133}$Xe, thereby enabling mass production of radioactive stents.

Thus according to its first aspect, the present invention provides a $^{133}$Xe radioactive stent for preventing restenosis of blood vessels that is prepared by ion injecting $^{133}$Xe into the entire surface of a cylindrical stent and which retards the growth of the smooth muscles of blood vessels by means of β-rays and internal conversion electrons emitted from the injected $^{133}$Xe.

According to its second aspect, the present invention provides a process for producing $^{133}$Xe radioactive stent for preventing restenosis of blood vessels which comprises performing ion injection of $^{133}$Xe on a stent positioned in a uniform irradiating unit within an ion injector, whereby $^{133}$Xe is uniformly injected into the entire surface of the stent.

According to its third aspect, the present invention provides a process for mass production of $^{133}$Xe radioactive stents for preventing restenosis of blood vessels, in which $^{133}$Xe that is a nuclear fission product generated upon irradiating $^{235}$U in fuel rods in a nuclear reactor with neutrons is supplied into an ion injector via a piping so that it is continuously ion injected into the surfaces of stents.

BRIEF DESCRIPTION OF THE DRAWINGS

FIG. 2 is a diagram showing how a nuclear reactor is connected to an ion injector.

Figure 1:
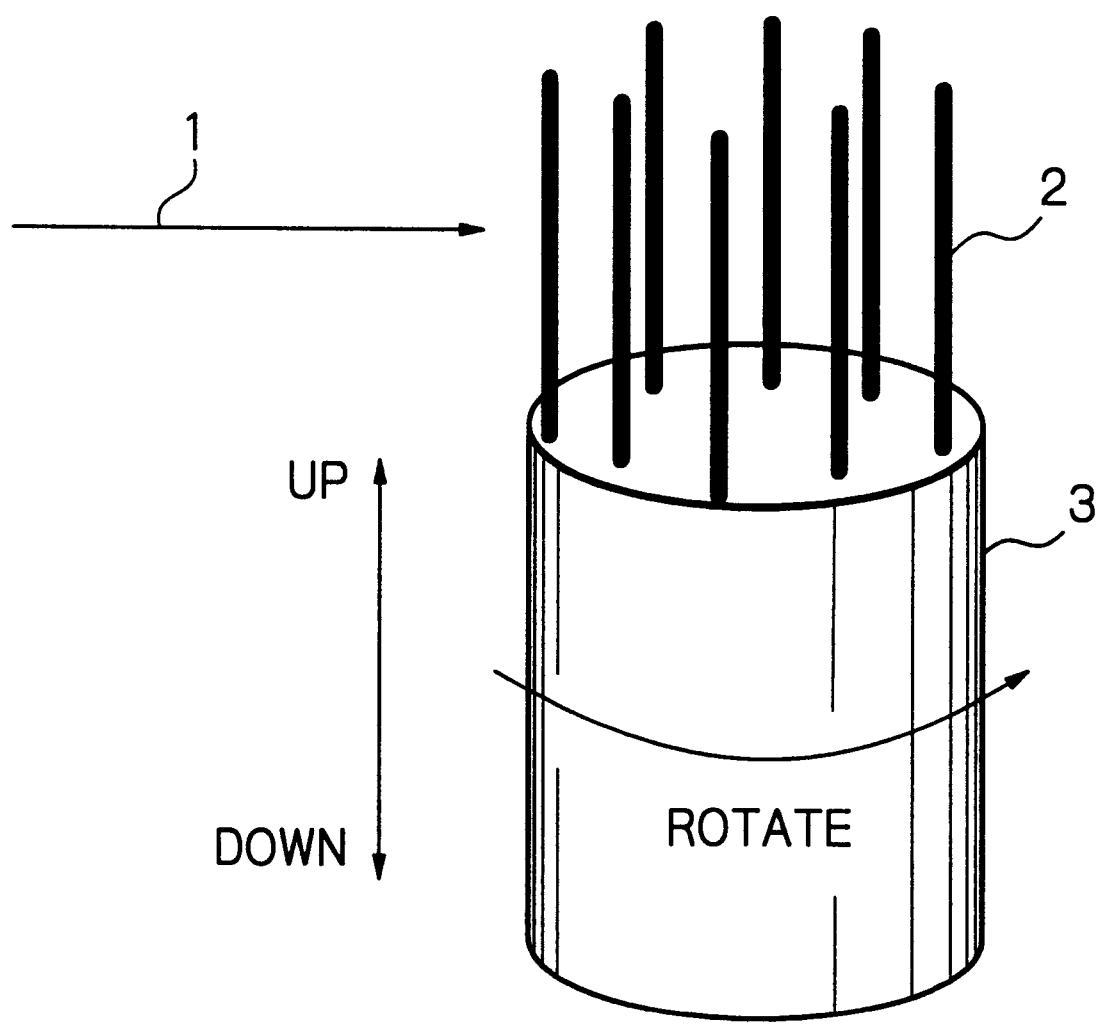
FIG. 1 is a diagram showing the irradiating portion of an irradiator capable of both rotation and vertical movements.

PREFERRED EMBODIMENT OF THE INVENTION $^{133}$Xe Radioactive Stent

In a half-life of 5.25 days, xenon-133 undergoes β-disintegration, whereupon it emits β-rays at a maximum energy of 350 keV, as well as 81 keV of γ-rays and internal conversion electrons due to γ-decay. This means that not only β-rays but also internal conversion electrons are expected to contribute to intravascular irradiation. In addition, due to their low energy, β-rays are only applied to intimae and will not affect other parts of the blood vessels. As a further advantage, $^{133}$Xe which is gaseous is easy to handle and has a higher ionization efficiency than $^{32}$p to be ion injected more efficiently with an ion injector.

Ion Injection with Ion Injector

As shown in FIGS. 1 and 2, ion injection is performed in vacuo with a uniform irradiating unit 10 provided within an ion injector 8 and this is in order to achieve uniform ion injection into the surfaces of cylindrical stents 2 made of stainless steel, tantalum or its alloys. Since the created ion beam has a larger diameter and a shorter length than the stents, uniform irradiation of the entire surface of each stent has to be assured by using a uniform irradiating unit equipped with a rotating table 3 capable of not only rotation but also vertical movements.

Connecting Nuclear Reactor to Ion Injector Xenon- 133 is a nuclear fission product which is constantly generated by nuclear fission in fuel rods in a nuclear reactor upon irradiation of 1$^{235}$U with neutrons. If the fuel rods are connected to an ion source 9 in the ion injector via piping, the gaseous $^{133}$Xe generated in the fuel rods can be transferred through the piping to the ion source in the ion injector. Radioactive stents can be mass produced by allowing the supplied $^{133}$Xe to be continuously ion injected into the surfaces of stents by means of the ion injector.

Stated more specifically, if neutrons impinge on $^{235}$U in the fuel rods 5 in the nuclear reactor 4, the resulting nuclear fission of $^{235}$U gives rise to $^{133}$Xe in a gaseous form. The generated $^{133}$Xe gas passes through the piping 6 to enter a Xe purifier 7, where it is worked up to the pure form. The pure $^{133}$Xe gas moves on through the piping 6 to be supplied into the ion source 9 within the ion injector 8. The supplied $^{133}$Xe gas is ionized to yield an ion beam, which is introduced into the irradiating unit 10 in the ion injector and directed to one of the stents positioned on the vertically movable rotating table 3 in the irradiating unit. Since the rotating table is capable of not only rotation on its shaft but also vertical movements, all stents erected on the table are uniformly irradiated with the ion beam, whereby $^{133}$Xe is uniformly injected into the surfaces of the stents.

The following example is provided for the purpose of further illustrating the present invention.

EXAMPLE

Gaseous $1^{33}$Xe (40 MBq) was transferred to a 3.8-L sample container via a vacuum line. The container was also charged with ca. 3 cm$^3$ of concentrated $^{129}$Xe isotope as a mass indicator in mass spectrometry. The container was connected to a Nielsen-type ion source in an ion injector, from which 40 keV or 60 keV of $^{133}$Xe was ion injected into the surfaces of stents each having a length of 14 mm and an outside diameter of 1.4 mm. To assure uniform irradiation of the surface of each stent, the ion injector was equipped with a vertically movable rotating irradiator (see FIG. 1).

While the $^{133}$Xe ion beam 1 was flying in a fixed path, the rotating table 3 not only moved vertically but also rotated, thereby permitting the $^{133}$Xe ion beam 1 to impinge uniformly on the surfaces of eight stainless steel stents 2 erected on the rotating table 3.

The radioactivities of the stents thus injected with $^{133}$Xe were measured with a Ge semiconductor detector and the results are shown in Table 1, from which one can see that stents having radioactivities of up to 98 kBq were produced by ion injection of $^{133}$Xe as a β-emitter.

TABLE 1

| Stent NO. | Radioactivity, kBq |
|---|---|
| 1 | 74.5 |
| 2 | 36.9 |
| 3 | 40.7 |
| 4 | 24.9 |
| 5 | 93.4 |
| 6 | 97.9 |

The radioactive stents produced by the above-described method were kept in place for 4 weeks in the abdominal aortas of rabbits; they proved to retard the growth of vascular smooth muscles.

FIG. 2 shows a general layout for connecting a nuclear reactor to the ion injector in such a way as to enable mass production of $^{133}$Xe radioactive stents. Xenon-133 produced in the fuel rods 5 in the nuclear reactor 4 passes through the piping 6 to enter the Xe purifier 7, where it is deprived of $^{131}$I and other impurities; the pure $^{133}$Xe also passes through the piping 6 to be transferred into the ion source 9 in the ion injector 8, where it is ionized and accelerated; the accelerated ion beam of $^{133}$Xe is injected into the surfaces of stents erected on the rotating table in the uniform irradiating unit 10 of the ion injector.

The $^{133}$Xe radioactive stents produced in accordance with the present invention proved to be capable of retarding the growth of vascular smooth muscles of the abdominal aortas of rabbits. Therefore, if such $^{133}$Xe radioactive stents are applied to patients suffering from arteriosclerosis, it is expected that they can retard the growth of vascular smooth muscles, thereby preventing the restenosis of opened blood vessels. If a uniform irradiator is employed in an ion injector connected to a nuclear reactor, radioactive stents featuring uniform irradiation with $^{133}$Xe can be produced in high volume.

What is claimed is:

1. A process of preparing a $^{133}$Xe radioactive stent to be placed within a blood vessel for preventing restenosis of the blood vessel by retarding the growth of smooth muscles by means of β-rays and internal conversion electrons emitted from $^{133}$Xe, the process comprising:

generating a gaseous nuclear fission product of $^{133}$Xe by nuclear fission in a $^{235}$U target in fuel rods in a nuclear reactor upon irradiation of $^{235}$U with neutrons;

flowing the gaseous $^{133}$Xe fission product into a Xe purifier;

supplying $^{133}$Xe from the Xe purifier into an ion source to ionize the $^{133}$Xe and yield an ion beam of $^{133}$Xe; and introducing the ion beam into an irradiating unit to irradiate stents positioned on a vertically moveable rotating table and to uniformly inject $^{133}$Xe into the surface of the stents.

* * * * *